PDF:/D:/0 DF/USS241875-20120814-DO(/US8241875-20120814-D00000.TIF unconvertible

US008241875B2

(12) United States Patent
Saito et al.

(10) Patent No.: US 8,241,875 B2
(45) Date of Patent: Aug. 14, 2012

(54) METHOD FOR PRODUCING FATTY ACIDS WITH AN IMMOBILIZED ENZYME PACKED COLUMN

(75) Inventors: Jun Saito, Kamisu (JP); Yoshitaka Senda, Kamisu (JP); Toshiteru Komatsu, Kamisu (JP)

(73) Assignee: Kao Corporation, Tokyo (JP)

( * ) Notice: Subject to any disclaimer, the term of this patent is extended or adjusted under 35 U.S.C. 154(b) by 1407 days.

(21) Appl. No.: 11/450,356

(22) Filed: Jun. 12, 2006

(65) Prior Publication Data

US 2006/0292675 A1    Dec. 28, 2006

(30) Foreign Application Priority Data

Jun. 21, 2005   (JP) .................. 2005-180455

(51) Int. Cl.
- *C12P 7/64* (2006.01)
- *C12N 11/14* (2006.01)
- *C12N 11/02* (2006.01)
- *C12N 11/08* (2006.01)

(52) U.S. Cl. ......... 435/134; 435/176; 435/177; 435/180

(58) Field of Classification Search ........................ None
See application file for complete search history.

(56) References Cited

U.S. PATENT DOCUMENTS

| 4,629,742 A | 12/1986 | Brady et al. | |
|---|---|---|---|
| 4,818,695 A * | 4/1989 | Eigtved | 435/134 |
| 5,010,004 A | 4/1991 | Kosugi et al. | |
| 5,032,515 A * | 7/1991 | Tanigaki et al. | 435/134 |
| 5,089,404 A * | 2/1992 | Matsumoto et al. | 435/134 |
| 5,219,744 A * | 6/1993 | Kurashige et al. | 435/135 |
| 5,292,649 A * | 3/1994 | Kosugi et al. | 435/136 |
| 6,258,575 B1 * | 7/2001 | Shimizu et al. | 435/134 |
| 6,921,652 B2 * | 7/2005 | Komatsu et al. | 435/135 |

FOREIGN PATENT DOCUMENTS

| EP | 1 004 662 A2 | 5/2000 |
|---|---|---|
| JP | A-61-85195 | 4/1986 |
| JP | A-01-98494 | 4/1989 |
| JP | A-05-95792 | 4/1993 |
| JP | 2001-169796 | 6/2001 |

OTHER PUBLICATIONS

U.S. Appl. No. 12/517,574, filed Jun. 04, 2009, Senda et al.
U.S. Appl. No. 12/518,285, filed Jun. 09, 2009, Saito et al.
J.Am. Oil Chem. Soc., 72: 1281, 1995.
J.Am. Oil Chem. Soc., 62: 1016, 1985.

* cited by examiner

*Primary Examiner* — David M Naff
(74) *Attorney, Agent, or Firm* — Oblon, Spivak, McClelland, Maier & Neustadt, L.L.P.

(57) ABSTRACT

A process for producing fatty acids, which comprises supplying an oil phase substrate and a water phase substrate to an enzyme column packed with an immobilized enzyme, concurrently flowing them in the same direction, and hydrolyzing a fat and/or oil, wherein the oil phase substrate and the water phase substrate are alternately supplied to the enzyme column.

8 Claims, No Drawings

METHOD FOR PRODUCING FATTY ACIDS WITH AN IMMOBILIZED ENZYME PACKED COLUMN

FIELD OF THE INVENTION

The present invention relates to a process for producing fatty acids in a manner of hydrolyzing a fat and/or oil with an enzyme.

BACKGROUND OF THE INVENTION

As a method for hydrolyzing a fat and/or oil with a fat and/or oil hydrolyzing enzyme such as lipase as a catalyst, there exists a conventional method that is performed by immobilizing an enzyme on a carrier, then allowing it to act on an oil-phase substrate and a water-phase substrate, with the aim of recovery and reuse of the enzyme. Methods for using an immobilized enzyme include the use thereof in a fluidized bed-type reactor (J. Am. Oil Chem. Soc., 72: 1281, 1995), the immobilization of an enzyme on a membrane to form a membrane type reactor (J. Am. Oil Chem. Soc., 62: 1016, 1985), and the packing of an immobilized enzyme, e.g., in a column to form a fixed bed (JP-A-61-85195, JP-A-01-98494, JP-A-05-95792, and JP-A-2000-160188). In the case of the fluidized bed-type reactor, however, there is a problem that the enzyme has not only a short durability but also a prolonged residence time. In the case of the membrane type reactor, on the other hand, there is a problem that the reaction rate is extremely low. Therefore, it has become common to use techniques which involve packing an immobilized enzyme, e.g., in a column to make a fixed bed, through which an oil phase substrate and a water phase substrate are then passed.

Such techniques include a method which is based on the counter current flow of the oil phase substrate and the water phase substrate (JP-A-61-85195, JP-A-01-98494, and JP-A-05-95792) and a method which is based on their concurrent flow (JP-A-2000-160188). The oil phase substrate and the water phase substrate are required to be uniformly mixed in order to effectively proceed with reaction because they are essentially immiscible with each other, and are generally made in the form of an emulsion. Alternatively, there is a method using a liquid-passing rate causing no emulsification because it is difficult for the emulsion particle to reach the enzyme adsorbed within a carrier (JP-A-61-85195).

SUMMARY OF THE INVENTION

The present invention provides a process for producing fatty acids in a manner of supplying an oil phase substrate and a water phase substrate to an enzyme column packed with an immobilized enzyme, then allowing them to concurrently flow in the same direction, followed by hydrolyzing the fat and/or oil, wherein the oil phase substrate and the water phase substrate are alternately supplied to the enzyme column.

DETAILED DESCRIPTION OF THE INVENTION

In the above-described method involving passing an oil phase substrate and a water phase substrate through a fixed bed consisting of an immobilized enzyme packed in an enzyme column to hydrolyze a fat and/or oil, there is a problem that the enzyme activity can not effectively develop because the flow of the reaction solution becomes inhomogeneous in the enzyme-packed column. This requires that the time of contact between the enzyme and the reaction solution be prolonged to enhance the reaction rate, thereby causing the problem that productivity (flow rate) is reduced.

Thus, the present invention provides a process for more efficiently producing fatty acids, which includes passing an oil phase substrate and a water phase substrate through a fixed bed having an immobilized enzyme packed in an enzyme column to hydrolyze a fat and/or oil, wherein the enzyme activity effectively develops to improve productivity.

As a result of analyzing the characteristics of the flow of reaction solution in an enzyme column packed with an immobilized enzyme, the present inventors have found that the oil phase substrate and the water phase substrate can flow in the same direction and alternately be supplied to the enzyme column to make uniform the flow of reaction solution to effectively develop the enzyme activity, resulting in improved productivity.

According to the invention, when the enzyme column packed with an immobilized enzyme is used in the hydrolysis of a fat and/or oil, good homogeneity of the flow of the whole reaction solution and effective development of the enzyme activity are made possible to produce fatty acids efficiently.

The immobilized enzyme used in the invention is an enzyme supported on a fixed carrier. Examples of the fixed carrier include inorganic carriers such as celite, diatomaceous earth, kaolinite, silica gel, molecular sieve, porous glass, activated carbon, calcium carbonate, and ceramics, and organic polymers such as ceramics powder, polyvinyl alcohol, polypropylene, chitosan, ion exchange resins, hydrophobic adsorption resins, chelating resins, and synthetic adsorption resins; ion exchange resins are preferable in terms of water-holding capacity. The ion exchange resin is preferably porous in that the large surface area thereof can provide an increased adsorption amount of enzyme.

The particle size of the resin used as the fixed carrier is preferably 100 to 1,000 μm, more preferably 250 to 750 μm. The pore size is preferably 10 to 150 nm. Examples of the material thereof include resins such as phenol formaldehyde, polystyrene, acrylamide, and divinylbenzene; phenol formaldehyde resin (for example, Duolite A-568 from Rohm and Hass) is preferable.

The enzyme used in the immobilized enzyme of the invention is not restricted, but a lipase as an enzyme for hydrolyzing a fat and/or oil is preferable in that its activity is effectively enhanced by a fat-soluble fatty acid and the like. The lipase may be any of commercially available lipases derived not only from animals or plants but also from microorganisms. Examples of the microorganism-derived lipase include that derived from the genus *Rizopus, Aspergillus, Mucor, Pseudomonas, Geotrichum, Penicillium*, or *Candida*.

According to the invention, it is essential that the enzyme be immobilized. The temperature for immobilizing the enzyme may be determined based on the characteristics of the enzyme, but is preferably 0 to 60° C. at which the inactivation of enzyme does not occur, more preferably 5 to 40° C. The pH of the enzyme solution used in the immobilization thereof may be within a range in which the denaturation of enzyme does not occur, and may be determined based on the characteristics of the enzyme as is the case with the temperature, but the pH is preferably 3 to 9. A buffer solution is used to maintain the pH; examples thereof include an acetate buffer, a phosphate buffer, and a Tris-hydrochloride buffer. It is preferable in terms of immobilization efficiency that the enzyme concentration in the above enzyme solution is not in excess of the solubility limit of the enzyme but sufficiently high. Also, the enzyme solution may optionally be a supernatant obtained by removing the insoluble part thereof using centrifugation, or the solution purified e.g. by ultrafiltration. The weight proportion of the enzyme used varies depending on the activity thereof, but is preferably 5 to 1,000 parts by weight, more preferably 10 to 500 parts by weight, based on 100 parts by weight of carrier.

When the enzyme is immobilized, it may be directly adsorbed to the carrier. However, it is preferable that the carrier is preliminarily treated with a fat-soluble fatty acid or a derivative thereof before the enzyme is directly adsorbed in order to absorb it in a state suitable to develop a high activity. The contact of the fat-soluble fatty acid or a derivative thereof with the carrier may be carried out by directly adding them to water or an organic solvent, or, for improving dispersibility, may be also performed by dispersing and dissolving the fat-soluble fatty acid or a derivative thereof in the organic solvent and then adding the solution to the carrier dispersed in water. Examples of the organic solvent include chloroform, hexane, and ethanol. The weight proportion of the fat-soluble fatty acid or a derivative thereof used is preferably 1 to 500 parts by weight, more preferably 10 to 200 parts by weight, based on 100 parts by weight of the carrier. The contact temperature is preferably 0 to 100° C., more preferably 20 to 60° C., and the contact time is preferably 5 minutes to 5 hours. The treated carrier is recovered by filtration, and maybe further dried. The drying is preferably carried out at a temperature of room temperature to 100° C., and may be performed under reduced pressure.

Of the fat-soluble fatty acid and a derivative thereof which are used to preliminarily treat the carrier, examples of the fat-soluble fatty acid include a saturated or unsaturated, straight-chain or branched fatty acid having 4 to 24, preferably 8 to 18, carbon atoms and optionally containing a hydroxyl group. Specific examples thereof include capric acid, lauric acid, myristic acid, oleic acid, linolic acid, α-linolenic acid, recinoleic acid, and isostearic acid. Examples of a derivative of the fat-soluble fatty acid include an ester or phospholipid of the fat-soluble fatty acid and a monovalent or polyvalent alcohol or saccharide, and the esters to which ethylene oxide is added. Specific examples thereof include a methyl ester, ethyl ester, monoglyceride, diglyceride, or ethylene oxide adduct thereof, polyglycerin ester, sorbitan ester, or sucrose ester of the above fatty acid. It is preferable for the step of immobilizing the enzyme on the carrier that any of these fat-soluble fatty acids and derivatives thereof is in the liquid form at ordinary temperature. These fat-soluble fatty acids and derivatives thereof may be used in a combination of two or more kinds, and may also be naturally-occurring fatty acids such as rapeseed-derived fatty acids and soybean-derived fatty acids.

The hydrolytic activity of the immobilized enzyme is preferably 20 U/g or more, more preferably 100 to 10,000 U/g, and even more preferably 500 to 5,000 U/g. Here, 1 U of the enzyme is defined as the hydrolyzing ability of the enzyme to generate 1 μmol of free fatty acid per minute when a mixture of fat and/or oil:water=100:25 (weight ratio) is subjected to hydrolysis while stirring and mixing at 40° C. for 30 minutes.

The hydrolytic activity of the immobilized enzyme imparted per unit weight of a fat and/or oil (U/g-oil) is almost inversely proportional to the amount of time required until a certain rate of hydrolysis is reached. When the hydrolysis is conducted using a packed bed (enzyme column) packed with the immobilized enzyme, although the hydrolysis rate varies depending on liquid feeding conditions (e.g. liquid-passing rate and temperature), the apparent activity (exhibiting activity) (U/g) of the immobilized enzyme is determined from the amount of time required for hydrolysis (residence time in the packed bed) and the weight (g-oil) of a fat and/or oil present in the packed bed and the packing weight (g) of the immobilized enzyme.

Examples of the oil phase substrate used in the invention include vegetable oils such as rapeseed oil, soya bean oil, sunflower oil, palm oil, and linseed oil, animal oils such as beef tallow, lard, and fish oil, or combined fat and/or oils thereof. These fat and/or oils may not only be deodorized oils but also fat and/or oils not preliminarily deodorized, but undeodorized oils are preferably used in part or whole of the fat and/or oils in that trans unsaturated fatty acids and conjugated unsaturated fatty acids can be reduced while leaving plant sterols, fatty acid esters of plant sterols, and tocopherol derived from the raw material fat and/or oils. In addition to the above fat and/or oil, an oil-soluble ingredient such as fatty acid may be mixed in the oil phase substrate.

The water phase substrate used in the invention is water, but a water-soluble ingredient such as glycerin may be mixed therein.

The enzyme column used in the invention may have any shape as long as it can endure the boost pressure of the pump used. It is preferable that the enzyme column has a jacket there around which can serve to adjust the reaction solution flowing in the column to a temperature suitable for the enzyme reaction. The temperature in the enzyme column is preferably set to 0 to 60° C., more preferably 20 to 40° C. in order to more effectively exhibit the activity of the immobilized enzyme. The length of the enzyme column may be set to a length necessary for obtaining a desired hydrolysis rate, but is preferably 0.01 to 10 m, more preferably 0.1 to 5 m, e.g. in view of reactivity and pressure loss in the column.

According to the invention, it is necessary that the oil phase substrate and the water phase substrate be supplied to an enzyme column packed with an immobilized enzyme and concurrently flowed in the same direction. Each of the substrates may be supplied to the enzyme column by a downward flow from the column top toward the column bottom or by an upward flow from the column bottom toward the column top.

The linear flow velocity (superficial velocity) of the reaction solution is preferably 1 to 400 mm/minute (0.017 to 6.67 mm/second), more preferably 5 to 200 mm/minute (0.083 to 3.33 mm/second). The linear flow velocity refers to a value expressed by the quotient provided by dividing a feed flow rate per minute (or second) ($mm^3$/minute or $mm^3$/second) (or also called $10^{-3}$ mL/minute) by a packed bed cross section ($mm^2$). It is preferred that the linear flow velocity is set to 400 mm/minute or less (6.67 mm/second or less) because an elevated pressure in the packing column due to an increased linear flow velocity makes liquid passing difficult and requires an increased pressure resistance of the enzyme-packing column and further may also cause the fragmentation of the immobilized enzyme. In addition, the linear flow velocity is preferably set to 1 mm/minute or more (0.017 mm/second or more) in terms of productivity. Because the exhibiting activity of the immobilized enzyme varies depending on the linear flow velocity, reaction conditions may be determined by selecting the optimal linear flow velocity to conduct a reaction commensurate with desired production capacity and production cost.

The residence time of the reaction solution in the enzyme column is preferably set to 30 seconds to 60 minutes, more preferably 1 to 40 minutes, even more preferably 1 to 30 minutes in that the equilibrium of the hydrolysis reaction is avoided to more effectively exhibit the activity of the immobilized enzyme to improve productivity. The residence time (minute) is represented by a value provided by multiplying the thickness (mm) of a packed bed by the void fraction thereof and then dividing the result by the linear flow velocity (mm/minute).

According to the invention, it is necessary that the oil phase substrate and the water phase substrate be alternately supplied to the enzyme column. A method for the alternate supply may be carried out by alternately supplying through separate or common piping directly connected to the enzyme column; however, the alternate supply through separate piping is preferable in terms of the avoidance of emulsification of the water and oil phases and ease of operation. Depending e.g. on the linear flow velocity and residence time of the reaction solution and, the timing at which the supply of the oil phase substrate and the supply of the water phase substrate to the enzyme column are alternately changed over (supply time) is preferably set, in terms of productivity, reactivity and the like, so that the time per single supply of each substrate is 10 seconds to 10 minutes, more preferably 30 seconds to 5 minutes.

In addition, when the thickness ($L_w$) of the water phase substrate in the enzyme column supplied at a time is represented by equation (1) below, $L_w$ is preferably set to the range of 5 to 150 mm, more preferably 15 to 120 mm in that the flow of the whole reaction solution in the enzyme column may be made uniform to effectively develop the enzyme activity to efficiently produce fatty acids.

$$L_w = (V_w/S) \times T_w \times (1/\epsilon) \quad (1)$$

[$V_w$: the feed flow rate of water phase (mm³/second), S: the cross section (mm²) of the enzyme column, $T_w$: the supply time (seconds) of the water phase, $\epsilon$: the void fraction of the packed bed]

Further, when the thickness ($L_o$) of the oil phase substrate in the enzyme column supplied at a time is represented by equation (2) below, $L_o$ is preferably set to the range of 10 to 250 mm, more preferably 30 to 220 mm in that the flow of the whole reaction solution in the enzyme column may be made uniform to effectively develop the enzyme activity to efficiently produce fatty acids.

$$L_o = (V_o/S) \times T_o \times (1/\epsilon) \quad (2)$$

[$V_o$: the feed flow rate of water phase (mm³/second), S: the cross section (mm²) of the enzyme column, $T_o$: the supply time (seconds) of the oil phase, $\epsilon$: the void fraction of the packed bed]

Further, the value of $L_w/L_o$ is preferably 0.1 to 10, more preferably 0.2 to 1 in that the flow of the whole reaction solution in the enzyme column may be made uniform to effectively develop the enzyme activity to efficiently produce fatty acids.

According to the invention, from a balance among the rate of reaction, productivity, and the like, the reaction solution itself having passed through the enzyme column may be a final reaction product, or the resultant reaction solution may be subjected to oil separation before again supplying to the same enzyme column in the same way as that described above, followed by a circular reaction until a desired reaction rate is reached. Alternatively, the above-described resultant reaction solution may be subjected to oil separation before again supplying to a separate enzyme column in the same way as that described above for conducting a consecutive reaction. For oil separation, the oil separator used is typically that e.g. of a spontaneous sedimentation type or centrifugation type, but not particularly restricted.

The following examples further describe and demonstrate embodiments of the present invention. The examples are given solely for the purpose of illustration and are not to be construed as limitations of the present invention.

EXAMPLES

Example 1

In a stainless-steel column (70 mm in internal diameter and 1,300 mm in packing height) equipped with a jacket was packed 1,210 g (dry weight) of immobilized lipase consisting of Lipase AY (Amano Pharmaceutical Co., Ltd.) immobilized on an ion exchange resin (Duolite A-568 from Diamond Shamrock), which was then maintained at 35° C. with the jacket. The hydrolytic activity of the immobilized lipase used was 3,154 U/g (dry weight). Rapeseed oil and distilled water were alternately fed from the top of the column to carry out a hydrolysis reaction. Conditions in the liquid feed operation were set to a feed flow rate of 77 mL/minute (1,283 mm³/second) and a supply time of 0.9 minute for each feed with the rapeseed oil, and to a feed flow rate of 77 mL/minute (1,283 mm³/second) and a supply time of 0.5 minute for each feed with the distilled water; the rapeseed oil and the distilled water were alternately supplied 126 times each so as to provide total supply amounts of 8,100 g and 4,860 g, respectively. The results of the hydrolysis reaction are shown in Table 1. The hydrolysis rates in the table were calculated by dividing each acid value determined by analysis by each saponification value.

Example 2

According to the method described in Example 1, conditions in the liquid feed operation were set to a feed flow rate of 77 mL/minute (1,283 mm³/second) and a supply time of 1.9 minute for each feed with the rapeseed oil, and to a feed flow rate of 77 mL/minute (1,283 mm³/second) and a supply time of one minute for each feed with the distilled water; the rapeseed oil and the distilled water were alternately supplied 63 times each so as to provide total supply amounts of 8,100 g and 4,860 g, respectively. The results of the hydrolysis reaction are shown in Table 1.

Example 3

According to the method described in Example 1, conditions in the liquid feed operation were set to a feed flow rate of 77 mL/minute (1,283 mm³/second) and a supply time of 5.5 minute for each feed with the rapeseed oil, and to a feed flow rate of 77 mL/minute (1,283 mm³/second) and a supply time of 3 minutes for each feed with the distilled water; the rapeseed oil and the distilled water were alternately supplied 21 times each so as to provide total supply amounts of 8,100 g and 4,860 g, respectively. The results of the hydrolysis reaction are shown in Table 1.

Comparative Example 1

In a glass stirring tank (substrate-supplying tank) equipped with a jacket were charged 8,100 g of rapeseed oil and 4,860 g of distilled water, followed by stirring at 400 rpm to prepare a reaction solution which was then fed using a metering pump from the top of the immobilized lipase-packed column described in Example 1. The feed flow rate was set to 77 mL/minute (1,283 mm³/second). The results of the hydrolysis reaction are shown in Table 1.

Comparative Example 2

A hydrolysis reaction was conducted in the same procedure as that in Comparative Example 1 except for the use of an immobilized lipase having a hydrolytic activity of 997 U/g (dry weight) whose packing amount was set to 1,220 g (dry weight) The results are shown in Table 1.

Comparative Example 3

The rapeseed oil and the distilled water were simultaneously fed without the preliminary mixing thereof from the top of the immobilized lipase-packed column described in Comparative Example 2 to conduct a hydrolysis reaction. The feed flow rate was set to 50 mL/minute (833 mm³/second) for the rapeseed oil and to 27 mL/minute (450 mm³/second) for the distilled water. The results of the hydrolysis reaction are shown in Table 1.

TABLE 1

|  |  | Example 1 | Example 2 | Example 3 | Comparative Example 1 | Comparative Example 2 | Comparative Example 3 |
|---|---|---|---|---|---|---|---|
| Activity of immobilized enzyme (U/g) | | 3154 | 3154 | 3154 | 3154 | 997 | 997 |
| Enzyme packing height (mm) | | 1177 | 1177 | 1177 | 1177 | 1180 | 1180 |
| Enzyme packing amount (g) | | 1210 | 1210 | 1210 | 1210 | 1220 | 1220 |
| Enzyme packing void fraction | | 0.58 | 0.58 | 0.58 | 0.58 | 0.56 | 0.56 |
| Feed amount (g) | rapeseed oil | 8100 | 8100 | 8100 | 8100 | 8100 | 8100 |
|  | distilled water | 4860 | 4860 | 4860 | 4860 | 4860 | 4860 |
| Feed flow rate (mL/min) | rapeseed oil | 77 | 77 | 77 | 77 | 77 | 50 |
|  | distilled water | 77 | 77 | 77 |  |  | 27 |
| Feed flow rate (mm³/sec) | rapeseed oil | 1283 | 1283 | 1283 | 1283 | 1283 | 833 |
|  | distilled water | 1283 | 1283 | 1283 |  |  | 450 |
| Supply time (min) at a time | rapeseed oil | 0.9 | 1.9 | 5.5 | — | — | — |
|  | distilled water | 0.5 | 1.0 | 3.0 |  |  |  |
| Feed amount (g) at a time | rapeseed oil | 64 | 267 | 267 | — | — | — |
|  | distilled water | 39 | 128 | 385 |  |  |  |
| Feed thickness (mm) at a time | rapeseed oil $L_o$ | 33 | 64 | 191 | — | — | — |
|  | distilled water $L_w$ | 17 | 35 | 103 |  |  |  |
| Hydrolysis rate (%) | | 81 | 83 | 80 | 76 | 68 | 64 |
| Apparent activity (U/g) of immobilized enzyme | | 624 | 746 | 586 | 468 | 326 | 276 |

Comparative Examples 1 and 2: the rapeseed oil and distilled water were mixed while stirring and then fed.
Comparative Example 3: the rapeseed oil and distilled water were simultaneously fed without preliminary mixing.

For conditions of feeding in the state of mixing rapeseed oil and distilled water or simultaneously feeding without the preliminary mixing thereof, the oil and the water were alternately subjected to intermittent supply to improve the hydrolysis rate, resulting in effective development of the (apparent) activity of the immobilized enzyme.

What is claimed is:

1. A process for producing fatty acids, comprising the steps of alternately supplying an oil phase substrate and a water phase substrate to an enzyme column packed with an immobilized enzyme, flowing the substrates in the same direction in said enzyme column, and hydrolyzing said oil phase substrate, wherein the water phase substrate supplied at a time in the enzyme column provides an immiscible layer having a thickness $L_w$ represented by equation (1) below and in the range between 5 and 150 mm:

$$L_w = (V_w/S) \times T_w \times (1/\epsilon) \quad (1); \text{ and}$$

wherein the oil phase substrate supplied at a time in the enzyme column provides an immiscible layer having a thickness $L_o$ represented by equation (2) below and in the range between 10 and 250 mm:

$$L_o = (V_o/S) \times T_o \times (1/\epsilon) \quad (2); \text{ wherein}$$

$V_w$ is the feed flow rate of the water phase (mm³/second), $V_o$ is the feed flow rate of the oil phase (mm³/second), S is the cross section (mm²) of the enzyme column, $T_w$ is the supply time (seconds) of the water phase, $T_o$ is the supply time (seconds) of the oil phase, and $\epsilon$ is the void fraction of the enzyme column, and wherein the value of $L_w/L_o$ is from 0.2 to 1.

2. The process for producing fatty acids according to claim 1, wherein the oil phase substrate is at least one selected from the group consisting of a vegetable oil and an animal oil.

3. The process of claim 1, wherein said immobilized enzyme is supported on a fixed carrier.

4. The process of claim 3, wherein said fixed carrier is an ion exchange resin having a particle size of 100 to 1,000 μm.

5. The process of claim 3, wherein said fixed carrier is a porous ion exchange resin having a pore size of 10 to 150 nm.

6. The process of claim 1, wherein said oil phase substrate and said water phase substrate are supplied to said enzyme column by a downward flow from a column top to a column bottom.

7. The process of claim 1, wherein said oil phase substrate and said water phase substrate are supplied to said enzyme column by a upward flow from a column bottom to a column top.

8. The process of claim 1, wherein said oil phase substrate and said water phase substrate have a linear flow velocity of 1 to 400 mm/minute.

* * * * *